United States Patent
Shimp et al.

(10) Patent No.: US 7,585,461 B2
(45) Date of Patent: Sep. 8, 2009

(54) TISSUE PATHOGEN INACTIVATION/REMOVAL PROCESS

(75) Inventors: Lawrence A. Shimp, Morganville, NJ (US); Sheldon Dean, Jackson, NJ (US); Daniel Martins, Freehold, NJ (US)

(73) Assignee: Osteotech, Inc., Eatontown, NJ (US)

( * ) Notice: Subject to any disclaimer, the term of this patent is extended or adjusted under 35 U.S.C. 154(b) by 784 days.

(21) Appl. No.: 10/766,614

(22) Filed: Jan. 28, 2004

(65) Prior Publication Data

US 2004/0219058 A1 Nov. 4, 2004

Related U.S. Application Data

(60) Provisional application No. 60/443,243, filed on Jan. 28, 2003.

(51) Int. Cl.
*A61L 2/18* (2006.01)
(52) U.S. Cl. ............................................. 422/28
(58) Field of Classification Search ................... None
See application file for complete search history.

(56) References Cited

U.S. PATENT DOCUMENTS

| | | | |
|---|---|---|---|
| 4,189,470 A | 2/1980 | Rose | 424/85 |
| 4,429,691 A | 2/1984 | Niwa et al. | 128/92 |
| 4,497,075 A | 2/1985 | Niwa et al. | 3/1.9 |
| 4,946,792 A | 8/1990 | O'Leary | 435/268 |
| 5,118,512 A | 6/1992 | O'Leary et al. | 424/549 |
| 5,120,656 A | 6/1992 | O'Leary et al. | 435/268 |
| 5,333,626 A | 8/1994 | Morse et al. | 128/898 |
| 5,507,810 A | 4/1996 | Prewett et al. | 623/11 |
| 5,513,662 A | 5/1996 | Morse et al. | 128/898 |
| 5,585,116 A | 12/1996 | Boniface et al. | 424/549 |
| 5,607,476 A | 3/1997 | Prewett et al. | 623/11 |
| 5,725,579 A | 3/1998 | Fages et al. | 623/16 |
| 5,730,933 A * | 3/1998 | Peterson | 422/22 |
| 5,779,815 A | 7/1998 | Briedohr et al. | 134/22.1 |
| 5,797,871 A | 8/1998 | Wolfinbarger, Jr. | 604/49 |
| 5,820,581 A | 10/1998 | Wolfinbarger, Jr. | 604/49 |
| 5,846,484 A | 12/1998 | Scarborough et al. | 422/28 |
| 5,976,104 A * | 11/1999 | Wolfinbarger, Jr. | 604/500 |
| 5,977,432 A | 11/1999 | Wolfinbarger, Jr. et al. | 623/16 |
| 6,293,970 B1 * | 9/2001 | Wolfinbarger et al. | 623/23.61 |
| 6,666,892 B2 | 12/2003 | Hiles et al. | 623/23.72 |
| 2002/0120345 A1 | 8/2002 | Anderson et al. | |

FOREIGN PATENT DOCUMENTS

| | | |
|---|---|---|
| WO | WO 91/11101 | 8/1991 |
| WO | WO 98/41245 | 9/1998 |
| WO | WO 01/19424 | 3/2001 |
| WO | WO 01/58497 | 8/2001 |
| WO | WO 03/065802 | 8/2003 |

* cited by examiner

*Primary Examiner*—Elizabeth L McKane
(74) *Attorney, Agent, or Firm*—Dorsey & Whitney, LLP

(57) ABSTRACT

Bone such as cortical or cancellous bone or connective tissue are centrifuged as a solution is applied to the tissue in a continuous process. The centrifuge creates forces, which cause the flowing solution to penetrate substantially all of the cavities of the tissue. The solution, which may be alcohol, a detergent, an oxidizer, or a surfactant, with or without water, flushes the cavities of the tissue and removes and inactivates viral and bacterial contaminants. In a second embodiment, bone or connective tissue is centrifuged in a batch process to remove contaminants from cavities in the tissue by first spinning the tissue dry and then submerging the tissue in a viral/bacteria cleansing solution and centrifuging the submerged tissue and solution at a sufficiently high speed and radius from the spin axis to create substantially high G forces on the tissue and solution to force the solution into and through the tissue cavities. The solution with the flushed contaminants is then removed from the vicinity of the tissue. In a further embodiment, an enzyme is centrifuged with the tissue to digest lipids and proteins which are then removed with a flushing solution which may also inactivate viral and bacterial contaminants. In yet a further embodiment, the centrifuge can be used to infuse biologically and/or structurally useful materials into the tissue. Further, the lipids and proteins may be removed by a chemically active agent such as oxo anions.

18 Claims, No Drawings

TISSUE PATHOGEN INACTIVATION/REMOVAL PROCESS

This application claims the benefit of provisional application Ser. No. 60/443,243 filed Jan. 28, 2003 entitled "Tissue Pathogen Inactivation/Removal Process", incorporated by reference herein in its entirety.

BACKGROUND OF THE INVENTION

This invention relates to a process for cleansing animal tissue and removal and or inactivation of pathogens in animal tissue such as human tissue including bone or any tissue, and more particularly, to cleansing the tissue for use as an implant.

It is desirable to physically clean a donor tissue of contaminants such as blood and to remove or inactivate potential pathogens (viruses, bacteria, fungi, mycoplasma and prions) for clinical use of the tissue such as bone as a grafting agent, or connective tissue that will be used to repair tendons or other connective tissue. The best way to accomplish this is to physically remove contaminants and pathogens as much as possible, then attack any remaining pathogens particles such as viruses and bacteria in the bone or connective tissue with one or more inactivating solutions.

During life, bone and connective tissue, whether it is allogenic, autogenic, or xenografic, is normally sterile with respect to bacteria. This is because the immune system keeps the body aseptic. Any significant build up of bacteria internally is abnormal and can quickly lead to death (sepsis). However, in the case of death, even from causes other than sepsis, bacteria can enter bone or connective tissue once life has ceased. The usual routes are migration from the digestive system or from degradation processes due to storage and handling. Therefore, bacteria that is present in recovered tissue tends to be more on the surface or in areas easily accessible from the surface.

Viruses, however, are more deeply imbedded. Unlike bacteria, viruses can be present throughout the body during life without causing fatal disease or even obvious sickness. Viruses enter tissue such as bone and connective tissue through the blood supply and can be present in capillaries deep within the internal cavities of the tissue, especially Haversian systems of bone.

The disinfecting processes normally employed to clean and disinfect bone and connective tissue prior to transplant are mainly topical, and do not penetrate deeply into bone or other tissues. As such, they are effective as topical disinfectants, but do not address potential internal viral contamination well. Sterilization is one option, but sterilization techniques typically damage bone and tissue when employed in the dose required to inactivate viruses.

A centrifuge may be employed as part of a bone cleaning system where the centrifugal forces and increased gravity force materials and substances from the bone in both a dry stage and a wet stage to remove bone marrow and cellular debris. This centrifuge action may provide effective cleaning/disinfecting for some contaminants and pathogens, but the present inventors believe that it does not treat viruses, especially those in the internal tissue cavities, effectively.

U.S. Pat. Nos. 6,682,695, 6,635,222 and 6,346,216 as well as published U.S. patent applications Ser. Nos. 20040013562, 20040013561, 20030213920, 20030186421, 20030185702, 20030180181, 20030162163, 20030161753, 20030124023, 20030095890, 20030064000, 20030059920, 20030059338, 20030049245, 20030031584, 20030031581, 20030012687, 20020155519 all disclose methods for sterilizing biological materials in which radiation protectants may be added to the material prior to the sterilization process. These protectants are so designed to as to reduce or prevent damage to the tissue during the radiation sterilization treatment. The present invention is a faster, more effective, thorough and efficient approach of introducing radiation protectants, cryoprotectants, mechanically useful substances, biologically useful substances or biologically active agents into the biological material such as tissue prior to or during the sterilization process compared to the previous methods.

The present inventors recognize that a much better approach is to use a cleansing and pathogen inactivation process that reaches all the internal spaces of the tissue and which removes or inactivates viruses. Internal bone spaces can be reached by a pressure/flow process employing pumps as disclosed in commonly owned U.S. Pat. No. 5,846,484, or a vacuum process as disclosed in commonly owned U.S. Pat. No. 5,513,662. Of interest also is published International application no. WO 00/29037

However, the patented processes are cumbersome to implement and use potentially unreliable liquid seals in a pressurized vessel. These patented systems are not desirable for these reasons.

SUMMARY OF THE INVENTION

According to an aspect of the present invention, a process for inactivating and/or reducing pathogens from tissue having a tissue axis and having a plurality of cavities in which pathogens reside comprises dry spin centrifuging the tissue at a given G force having a given direction to remove material from the tissue and/or promote solvent penetration into the tissue and at least one further centrifuging step using a solvent fluid to inactivate or reduce pathogens in the tissue. During the at least one further centrifuging step, the process includes: orienting the tissue axis to an angle non-parallel to the G force given direction, the G force being greater than 1000 G to thereby penetrate the pathogen reducing solvent fluid into substantially all of the cavities of the tissue where the pathogens reside to inactivate and/or reduce the pathogen content in the cavities.

In a further aspect, the process comprises exposing the tissue to a volume of the solvent of at least 3 liters during a centrifugation step.

In a further aspect, the solvent fluid is selected from at least one of the group consisting of an alcohol, a detergent, an oxidizer, a solvent and a surfactant.

In a further aspect, the process comprises centrifuging the tissue in at least a portion of the process in the presence of the solvent fluid at a G force greater than 4000 G.

In a further aspect, a process for inactivating and/or reducing pathogens in tissue having a plurality of cavities in which the pathogens reside comprising centrifuging the tissue with a pathogen reducing solution in a single wet spin to produce a G force on the material to remove material from the tissue and promote solution penetration into the tissue, the centrifuging penetrating the pathogen reducing solution into substantially all of the cavities of the tissue where the pathogens reside to thereby inactivate and/or reduce the pathogen content in the cavities.

In a further aspect, the centrifuging with the pathogen reducing solution may be continuous or batch.

In a further aspect, the process includes dry centrifuging the tissue prior to centrifuging the pathogen reducing solution to remove traces of solvents and debris.

Preferably, the tissue comprises at least one of cancellous and cortical bone and connective tissue.

In a further aspect, wherein the solvent reducing solution comprises at least one viral and/or bacterial pathogen inactivating solution to inactivate the pathogens.

In a further aspect, the tissue comprises bone, the pathogens comprise lipids and/or proteins, the solvent reducing solution comprises substances for removing the lipids and/or proteins from the bone, the process comprises continuously flowing and centrifuging the pathogen reducing solvents and/or surfactants with the bone so that the solvents and/or surfactants continuously infuse into and out of the cavities of the bone to continuously flush the lipids proteins and/or pathogens from the bone.

In a further aspect, a process for cleaning animal tissue having cavities and including contaminating material which interferes with penetration of the tissue cavities by fluids, the tissue defining a longitudinal axis, comprises centrifuging the tissue in a batch centrifuge first in a dry state to remove the contaminating material to promote penetration of fluids into the tissue cavities, followed by at least two centrifuging steps each producing a G force in a given direction on the tissue and using at least one solvent to bring about inactivation and/or removal of bacterial and/or viral contaminants in the tissue, the tissue axis being oriented in a given orientation relative to the G force given direction and wherein the G force of each step is at least 1000 G.

In a further aspect, the tissue is bone, the bone axis being oriented parallel to the G force direction.

In a further aspect, the tissue axis is non-parallel to the G force direction.

A still further aspect, includes dry centrifuging of the tissue to remove the at least one solvent from the tissue and for removing contaminants separated by the centrifuging from the vicinity of the tissue.

In a still further aspect, a process is provided for infusing biologically and/or mechanically useful substances into tissue such as cryoprotectants, radiation protectants, plasticizers and polymers.

In a further aspect, a process for introduction of at least one biological agent in animal tissue comprises centrifuging the tissue in the presence of a liquid containing the at least one growth factor. A list of biological agents that may be used in the present invention is included as Appendix A.

Definitions:

"Pathogens" as used herein are any undesirable foreign or infectious agents (e.g. microbes, viruses, bacteria, fungi, prions, mycoplasma, etc.) particularly those tissue contaminants which may preclude using the tissue as a transplant in the body of an animal.

The term "dry state" as used herein describes the absence of additional exogenous moisture or liquid. A tissue is considered to be in the "dry state" if no additional exogenous moisture or liquid has been added. For example, a tissue is in the "dry state" when it is free from a liquid carrier, solvent reducing solution, or other liquid used in the invention.

"Penetrating solution" as used herein, means any solution, solvent, or liquid or mixture that is capable of contacting at least a portion of the interior of a biological material, such as a tissue.

"Pathogen reducing solution, and Inactivation solution" as used herein mean any solution, solvent, or liquid which is capable of reducing the number of pathogens or inactivating the pathogens present on or in a biological material.

"Protectant" as used herein means any substance or material which prevents, reduces or eliminates undesirable damage to a biological material or any substance which enhances, strengthens or otherwise increases a property of the biological material.

"Mechanically useful substance" as used herein means any substance or material which prevents, reduces or eliminates undesirable mechanical damage to a biological material or any substance which enhances, strengthens or otherwise increases a mechanical property of the biological material.

"Biologically useful substance" any substance or material, which prevents, reduces or eliminates undesirable biological damage to a biological material or any substance which enhances, improves or otherwise increases a biological property of the biological material.

"Chemically reactive substance" any substance or material, which reacts with a component of the biological material to prevent, reduce or eliminate an undesirable property or any substance which enhances, improves or otherwise increases a desirable property of the biological material through a chemical reaction.

"Cryoprotectant" any substance or material which prevents or reduces undesirable damage to a biological material caused by lowering the temperature of a biological material or any substance or material which enhances, strengthens or otherwise increases the ability of the biological material to withstand lowered temperatures.

"Radiation protectant" or "Radioprotectant" any substance or material which prevents or reduces undesirable damage to a biological material caused by the irradiation of a biological material or any substance or material which enhances, improves or otherwise increases the ability of the biological material to withstand irradiation.

"Lowered temperature" as used herein means any temperature below ambient temperature.

"Increased, raised or elevated temperature" as used herein means any temperature above ambient temperature.

"Tissue axis" as used herein refers to the longitudinal axis of a tissue, which has a length that is greater than its other dimensions. A longitudinal axis may also be defined by the general fiber direction such as the collagen fiber direction in cortical bone.

"Effective weight" as used herein refers to the weight of any object, liquid, or material when it is subjected to increased G forces above 1 G.

DETAILED DESCRIPTION OF THE INVENTION

The present invention provides a process for cleaning tissue and inactivating and/or reducing pathogens from tissue having a tissue axis and having a plurality of cavities in which pathogens reside which comprises dry spin centrifuging the tissue at a given G force having a given direction to remove material from the tissue and/or promote solvent penetration into the tissue and at least one further centrifuging step using a solvent fluid to inactivate or reduce pathogens in the tissue. The tissue axis refers to the longitudinal axis of a tissue which has a length dimension that is greater than its other dimensions. The longitudinal axis is defined by that length dimension.

The centrifugal created pressurization has the advantage of avoiding the need for cumbersome and potentially unreliable liquid seals in a pressurized vessel used in other methods to keep pressurized liquid inside the bone during the treatment process, as well as generating much higher effective pressures/pressure differentials than can be generated by conventional pumps and seals, or by a vacuum. It can also be readily applied to connective tissue, which is difficult to treat with the previously disclosed pressure/flow process.

The centrifuge action spins the tissue being treated to create an artificial increased gravity (G) force across the tissue. Centrifugal G forces are a linear function of the spin diameter and a square function of the RPM of the spun material (Relative Centrifugal Force=1.12 (radius in mm) (RPM/1000)$^2$. When a tissue such as a bone is spun in a centrifuge, it and all its internal components become substantially "heavier" than normal due to the result of the applied G forces. If the G force generated is, for example 2000, this means the effective weight of the tissue and contaminants is also increased by 2000 times. The G forces may range to any value higher than 1000, for example to about 4000 G or greater depending upon the material being centrifuged or the desired penetration rate. By dry spinning a bone or a fragment of bone (with no additional fluid, such as a treatment liquid, present around it) the non-bone or non-tissue "movable or flowable" internal contaminating components, such as blood, lipid, liquids, water, and viruses, become substantially heavier than in the absence of the centrifugal forces. As a result, these components begin to flow out of the bone in response to the centrifugal forces thereon. The centrifuge may contain any type of rotor (for example, a fixed angle rotor, a swinging bucket rotor, or a continuous flow rotor. The rotor may be selected based upon the desired application as described herein.

Under normal circumstances, a bone, for example, can be held vertically and the so called "movable" contaminants will not typically separate from the bone in response to the force of gravity. In a first dry spin phase centrifuge action according to one aspect of the present invention, most of the "moveable or flowable" contaminating components in or on a tissue will flow out of the tissue. This dry spin process, i.e., no other fluid treatment liquid materials are used at this time, initially removes a majority of the virus particles and the fluids (blood) where they are normally located.

In a second fluid treatment phase, inactivation by alcohol, detergent, or other solutions, is required to treat the remaining pathogens and contaminants. Such inactivation requires that the treatment inactivation solution penetrate the tissue, e.g., bone, and contact remaining viral particles throughout the tissue. This penetration occurs with a centrifugal action by at least partially submerging the tissue in a liquid treatment solution, then spinning the liquid and tissue in the centrifuge. During the spin cycle, the tissue is at least partially submerged in the treatment fluid. Because the G forces proportionately increase with the spin radius and RPM, a G force gradient will be set up over the tissue from the portion nearest to the spin axis, e.g., the center of the centrifuge rotor, to the portion nearest the radially outermost peripheral surface of the tissue. Thus the fluid will exhibit a increased "effective weight" and there will exist a gradient of G forces extending increased G forces in a direction radially outwardly from the spin axis and a pressure gradient will be set up that provides a driving force for the fluid to penetrate the bone or other tissue. The penetration is facilitated by the initial removal of the mobile contaminants under the centrifuge G force field in the prior first dry spin phase.

The solutions used during the centrifuge may have volumes of about 3 liters or more, e.g., more than 5 liters.

As the inactivation fluid penetrates the tissue during the spin cycle, it displaces air (in empty cavities) liquids or particles in filled cavities. Displaced materials that are lighter than the inactivation liquid entering the cavities (such as air and lipid) rise to the top of the treatment fluid, while heavier liquids and objects will fall to the bottom of the container. Contaminating materials that are soluble in the treatment inactivation fluid will dissolve in the fluid. (These would be removed in the continuous flow process.)

If the tissue such as bone has not been completely cleaned previously by the first phase dry spin, penetration and displacement will still occur, but will be slower, and the lighter contaminating components (such as lipid) will rise above the bone and collect in a high concentration that may recontaminate the bone upon removal from the centrifuge. Also, materials that are soluble in the treatment liquid fluid will remain within the bone cavities (in a solubilized state). Carrying out a "dry spin" or additional wetspins after the liquid treatment will help to remove these solubilized contaminants.

In one alternative, the tissue may be treated in a continuous process mode rather than in the batch process mode described above. In the continuous centrifuge mode, the treatment fluid is continuously flowed into the centrifuge and the treatment fluid that is continuously removed from the centrifuge carries contaminants and waste materials. The flow helps to remove lighter contaminants from the centrifuge (especially if these components are soluble or partially soluble in the treatment inactivation liquid which also serves as a rinsing agent), while heavier contaminants, instead of collecting in the bottom of the centrifuge container (e.g. bucket, tube, or vial) as in the batch process, are essentially 100% removed in the continuous flow process. This is accomplished by running the process for a time period that is empirically or analytically measured for each tissue type and size, e.g., bone or connective tissue, and shown to remove the contaminants or reduce contamination to any desirable level. An in-line or secondary analytical monitoring device may be used with the continuous flow process to determine when the inactivation liquid or other solution is free of contaminants (e.g., real time or other PCR device, tissue culturing, bacterial culturing, plaque assay, XTT assay using Sodium 3'-[1-[(phenylamino)-carbonyl]-3,4-tetrazolium]-bis(4-methoxy-6-nitro)benzene-sulfonic acid hydrate, or the MTT assay using yellow tetrazolium salt [3-(4,5-Dimethylthiazol-2-yl)-2,5-diphenyltetrazolium-bromide] ELISA (enzyme linked immunosorbent assay), or FACS (fluorescence automated cell sorting)). Optionally, chemical materials in the inactivation liquid or other solution may be monitored (e.g., pH. concentration and composition) either in-line or with a secondary analytical monitoring device (e.g., HPLC (high performance liquid chromatography) mass spectroscopy, ICP-AES (inductively coupled plasma-atomic emission spectrometry), ICP-MS (inductively coupled plasma-mass spectrometry, GCMS (gas chromatograph-mass spectrometer), and MALDI-TOF MS (matrix-assisted laser desorption/ionization-time of flight mass spectrometry, and atomic absorption.

Although both the batch (a static flow process) and continuous flow modes are effective, the continuous flow mode reduces the chance of back contamination from removed materials and facilitates automated fluid changes without having to stop and empty centrifuge tubes, bottles or buckets. A combined continuous and batch process can be carried out using different centrifuges for each type of step, or by using a continuous flow centrifuge with provisions for stopping the fluid flow at will. The fluid flow must be stopped at both the entrance and exit points. In this situation, the continuous flow centrifuge operates as a batch centrifuge which is desirable for conserving fluid during the penetration stage, or when performing an enzyme treatment, enzymatic digestion, other incubation time, protectant treatment, or plasticizing treatment is being carried out. Once the "batch" step is completed, the fluid flow can be resumed in a continuous mode and the residues flushed out.

When full permeation of the bone is desired, there are minimum G forces necessary to obtain full permeation within a reasonable time, e.g., in excess of 1000 G. Minimum dry-spin conditions also exist to about 1000 G.

Tissue such as bone, which may have a longitudinal axis as defined by the fiber direction such as in cortical bone, can be oriented in a regular or random way in a centrifuge, i.e., with the bone axis parallel to or non-parallel to the centrifuge G force direction. Orientation applies more specifically to cortical (dense) bone. Cancellous (porous) bone is generally anisotropic and so direction matters little. Cortical bone, however, has a more directional fibrous structure with mineralized collagen fibers running generally parallel to the medullary canal. There is also an internal blood circulation system in cortical bone that runs vertically and horizontally relative to the medullary canal direction in a long bone such as the femur or tibia, for example, while cancellous bone only has an external circulation system (that runs through the macropores in the cancellous structure). In some embodiments, it may be preferable to orient the bone to maximize or improve efficiency of the penetration of solutions into tissue. This may be determined by conducting a permeation test centrifugation using a detergent or alcohol, which comprises a dye. After conducting a spin with the experimental parameters, dye solution and tissue orientation, the tissue may be examined for dye penetration by histological cross-section analysis.

The objective is to remove contaminants and marrow elements (blood and lipid) from the macroporous cancellous bone as well as the contents of the internal canals (Haversian canals) in cortical bone (e.g. pathogens, blood, and lipid).

Centrifugal G forces of the desired magnitude result in flows of the cleansing solution or solutions into all of the internal spaces in bone, regardless of the bone orientation.

Increases in G force reduced the time needed for penetration of solutions into bone. However, there is also a practical upper limit to the centrifuge G force that is set by the threshold of bone damage. Where bone damage is not desirable or acceptable, a test centrifugation may be preformed with the G force, time and solutions of the cleaning process. After centrifugation, the tissue maybe examined histologically and mechanically to determine if unacceptable damage occurred during the process. Where tissue damage is not a concern, G force and time may be increased to any desired force and time to achieve desired penetration and inactivation. Cortical bone is stronger than cancellous bone, and the cortical bone is strongest in compression. Typical maximum sustainable compressive loads for cortical bone are 60 to 100 MPa, which corresponds to a G force of about 31000 G (assuming an average bone density of 2 g/cc and that the medullary canal is perpendicular to the axis of rotation). In other loading conditions, calculations are not so straight forward. For instance, in a fixed angle rotor or randomly loaded centrifuge, the forces acting on the bone will not be ones of pure compression. There can be bending loads applied to longer bone pieces that are not evenly supported along their length, or point contacts where a sharply curved bone surface lies against a flat or a wide radius curved surface in the centrifuge. In these cases where damage is not desirable or acceptable, experimentation to determine the threshold of damage to the bone may be carried out in order to establish a range of safe G forces. For cancellous bone, the minimum compressive strength is about 3 MPa. This corresponds to a G force of about 3250 G assuming the bone is a single piece (or a stack of pieces) about 100 mm high.

Where damage to the bone is not desirable or would be unacceptable, the maximum force that can be applied to cancellous bone is much less than the force that can be applied to cortical bone, even if the cortical bone is not optimally loaded. Cortical bone pores and cavities are also much harder to penetrate than cancellous bone, so optimum treatment cycles for cortical and cancellous bone will be different. However, it is still possible to treat the two bone types together as long as the conditions chosen are satisfactory for the weakest bone present. Again. If damage to the tissue is not a concern, any G force or time can be used. Empirical studies are used to optimize the centrifuge process for the type of tissue being treated with respect to damage, process time, and process efficiency. Such studies are within the skill of those of ordinary skill in this art for example a solution comprising a dye may be used in the centrifugation process. After centrifugation the tissue such as bone may be examined histological cross section. Mechanical tests such as strain, creep and mechanical strength may also be determined. Examples of possible ways to minimize loading damage are to provide a series of partitions, shelves, shelf supports, sponges, protective cages or other suitable tissue holders within the centrifuge vessel to prevent large stacks of bone, tissue or other biological material from forming. In one embodiment, weaker cancellous bone may be stacked on top of stronger cortical pieces, and limiting the maximum G force of the process. In some embodiments, suitable tissue holders ensure that the contaminants are kept away from the tissue while permitting solvents and solutions to flow freely. In other embodiments it may desirable to use tissue holders with selectively permeable membranes or barriers which permit particles of certain sizes to flow through, or restrict the direction of particle or liquid travel to only one direction. Such barriers include but are not limited to, filters and dialysis membranes.

The main advantage of using a centrifuge in bone processing is the increased penetration of inactivating/cleansing/protective/plasticizing fluids. Additionally, use of the centrifuge is a "faster", more efficient, thorough, more effective method to achieve penetration compared to other methods. The centrifuge can be used alone for a penetration step, or to carry out a complete treatment process. Treatment steps are preferably, a dry spin to remove loose contaminants/blood/lipids, a sequential or combined penetration treatment with one or more inactivating solutions such as a detergent or alcohol (which may be done by spinning or other method, e.g., sonication, agitation), and a dry spin to remove residues of the inactivating solution. Optionally, an enzyme treatment using an enzyme such as a lipase or a protease to remove or modify all or selected lipids or proteins can be added to the process to aid in cleaning, preparing and processing the tissue. Optionally, a protectant such as glycerol, or an antioxidant may be added to the process to treat the tissue. The protectants may be introduced by batch or continuous centrifugation, sonication, incubation or vacuum/pressure flow.

Additional steps such as a deep cleansing step using a solvent or detergent, preferably in a continuous flow centrifuge, can be added as well as a penetration step using any type of inactivating solution such as a peroxide or an acid, or cryoprotectants, or biologically useful substance.

In some embodiments, it is possible to carry out some steps partially in the centrifuge and partially outside the centrifuge. For example, a penetrating solution can be infused into the bone using a centrifuge, then the bone can be removed from the centrifuge and allowed to sit while the solution acts on viruses/bacteria/lipids or proteins in the bone. Alternatively, the bone, tissue or other biological material may be incubated at any temperature, pressure, or p.H. which is desirable for the given reaction. Such temerature may be 37° C. or ambient temperature and such atmospheric pressure may be 1 atmosphere for certain enzymatic reactions. For other reactions, p.H., temperature and pressure may be higher or lower. Alternatively, the centrifuge can be used just for removal of contaminants in a dry spin cycle.

In one alternative, a process for removing lipids and/or proteins from bone may be implemented by centrifuging the bone in the presence of one or more enzymes (e.g. lipases and proteases) which digest the lipids and/or proteins to make them more soluble. The bone is at least partially submerged in a fluid containing the enzymes. Such enzymes are well known to those of ordinary skill in this art (e.g., trypsin, papain, furin, pepsin, etc.). The centrifuging action creates G forces sufficient to force or infuse the enzymes into substantially all of cavities of the bone. The enzymes are used to digest the lipids and/or proteins that coat the pathogens to make them more soluble. Additionally, temperature, p.H. and pressure may be varied to control the rate of enzymatic or chemical reactions. After the digestion process is completed, which can be determined empirically or analytically for individual bone specimens, the residues are removed by the batch or continuous flow processes described above.

As a result, a practical, efficient process is disclosed for cleaning and inactivating/removing pathogens from bone or other tissue for transplantation while infusing useful substances. Compared to a rinsing type of pressure/flow process alone, the centrifuge process provides increased pressure gradients while minimizing fluid usage and hydraulic complication. Compared to an ultrasonic bath type process, the centrifuge gives greater penetration in a shorter period of time.

Mechanically useful substances may be added to enhance the process. Such mechanically useful substances include polymers which can be set by heat, chemical reaction, solvent removal, extraction or evaporation to structurally add to the strength of the tissue or otherwise enhance the mechanical properties of the tissue. The mechanically useful substances may be added by infusing polymers and the like into the tissue during the centrifuge operation or incubation steps and the solvent removal, extraction or evaporation may occur during the centrifuge operation or at some other time before or after centrifugation. Further, chemically reactive substances may also be infused into the tissue. The chemically reactive substances such as oxidizing agents break down lipids and/or proteins in the tissue cavities. Such chemically active agents include oxo anions derived from peroxides, free radicals, and the like.

Other useful substances that can be infused by the current invention are biological agents as included in Appendix A, cryopreservatives such as glycerol and mannitol that inhibit ice crystal formation, dimethyl sulfoxide, propylene glycol, liquid carbon dioxide, fish blood glycoproteins isolated from species of the genus *Trematomus* or *Borchgrebinki arachis*, formamide, polyvinyl pyrrolidone, trehalose, hydroxyethyl starch, plasticizers such as carboxy methyl cellulose, other polyhydroxy compounds, for example, 1,4,-butylene glycol, diethylene glycol, triethylene glycol, tetraethylene glycol, dipropylene glycol; polyoxyethylene-polyoxypropylene copolymer, e.g., of the type known and commercially available under the trade names Pluronic and Emkalyx; polyoxyethylene-polyoxypropylene block copolymer, e.g., of the type known and commercially available under the trade name Poloxamer; alkylphenolhydroxypolyoxyethylene, e.g., of the type known and commercially available under the trade name Triton, and the like. Polyhydroxy ester, for example, monoacetin, triacetin, poly(oxyalkylene) glycol ester, and the like. Other useful substances that can be infused are fatty alcohols, for example primary alcohols, usually straight chain having from 6 to 13 carbon atoms, including caproic alcohol, caprylic alcohol, undecyl alcohol, lauryl alcohol, and tridecanol. Other useful substances that may be used in the invention are fatty alcohol esters, for example, ethyl hexyl palmitate, isodecyl neopentate, octadodecyl benzoate, diethyl hexyl maleate, and the like. Additionally, fatty acids having from 6 to 11 carbon atoms, for example, hexanoic acid, heptanoic acid, octanoic acid, decanoic acid and undecanoic acid may be used. Fatty acid esters, for example, polyoxyethylene-sorbitan-fatty acid esters; e.g., mono- and tri-lauryl, palmityl, stearyl, and oleyl esters; e.g., of the type available under the trade name Tween from Imperial Chemical Industries; polyoxyethylene fatty acid esters; e.g., polyoxyethylene stearic acid esters of the type known and commercially available under the trade name Myrj; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol; e.g., of the type known and commercially available under the trade name lmwitor; sorbitan fatty acid esters, e.g., of the type known and commercially available under the trade name Span, including sorbitan-monolauryl, -monopalmityl, -monostearyl, -tristearyl, -monooleyl and trioleylesters; monoglycerides, e.g., glycerol mono oleate, glycerol mono palmitate and glycerol monostearate, for example as known and commercially available under the trade names Myvatex, Myvaplex and Myverol, and acetylated, e.g., mono- and di-acetylated monoglycerides, for example as known and commercially available under the trade name Myvacet; isobutyl tallowate, n-butylstearate, n-butyl oleate, and n-propyl oleate could also be used with the invention. Liquid silicone, for example, polyalkyl siloxanes such as polymethyl siloxane and poly(dimethyl siloxane) and polyalkyl arylsiloxane may also be introduced into tissue using the current invention. Useful polyhydroxy agents possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, carrageenan, agar, alginic acid, guar gum, gum tragacanth, locust bean gum, gum arabic, xanthan gum, amylose, mixtures of any of the foregoing, and the like. Additionally, substances that protect against radiation damage if the bone or tissue is to be irradiated in a subsequent step may be used. Such radioprotectants include, but are not limited to, anti oxidants.

There thus has been described a process for inactivating pathogens in tissue having a plurality of cavities in which pathogens reside by centrifuging at least one pathogen reducing solution into substantially all of the cavities of the tissue where the pathogens reside to thereby reduce the pathogen content in the cavities.

Also shown is a process for inactivating and/or reducing pathogens from tissue having a tissue axis and having a plurality of cavities in which pathogens reside comprising dry spin centrifuging the tissue at a given G force having a given direction to remove material from the tissue and/or promote solvent penetration into the tissue and at least one further centrifuging step using a solvent fluid to inactivate or reduce pathogens in the tissue. During the at least one further centrifuging step, included is the step of orienting the tissue axis to an angle non-parallel to the G force given direction, the G force being greater than 1000 G to thereby penetrate the pathogen reducing solvent fluid into substantially all of the cavities of the tissue where the pathogens reside to inactivate and/or reduce the pathogen content in the cavities The process described also includes spinning the tissue in at least a portion of the process in the presence of a tissue cleansing fluid at a G force greater than 1000 G and preferably in the range to 4000 G or greater.

There also thus has been shown a process wherein during centrifuging, the tissue is preferably exposed to a volume of at least one cleansing solution of at least 3 liters and which may be about 4 or 5 liters, for example.

There also has been shown a process for dry centrifuging the tissue after centrifuging the at least one solution to remove traces of solvents and debris, such as dry centrifuging the tissue prior to centrifuging at least one solution to remove at least one of blood, lipid, and proteins or all.

Further, there has been shown at least one solution that comprises at least one viral and/or bacterial pathogen inactivating solution to inactivate the pathogens such as bacteria or viruses that may reside in the cavities of the tissue such as bone or connective tissue.

There also has been shown a process wherein the centrifuging for flowing the at least one solution flushes the pathogens from the cavities and inactivates the pathogens in the cavities and then removes the at least one solution carrying the flushed pathogens from the vicinity of the tissue. Further, in one aspect, the solvents and/or surfactants are continuously infused into and out of the cavities of bone to continuously flush the lipids and/or proteins from the bone.

A process is also described for cleaning animal tissue having cavities and including contaminating material which interferes with penetration of the tissue cavities by fluids, the tissue defining a longitudinal axis, the process comprising centrifuging the tissue in a batch centrifuge first in a dry state to remove the contaminating material to promote penetration of fluids into the tissue cavities, followed by at least two centrifuging steps each producing a G force in a given direction on the tissue and using at least one solvent to bring about inactivation and/or removal of bacterial and/or viral contaminants in the tissue, the tissue axis being oriented in a given orientation relative to the G force given direction and wherein the G force of each step is at least 1000 G.

A further process may include infusing biologically and/or mechanically useful substances into tissue using the processes described above For example, the biologically useful substances include at least one antibiotic or a tissue preservative during storage of the tissue or at least one tissue growth factor for release from the tissue after implantation of the tissue into an animal.

The mechanically useful substances include plasticizers that assist the tissue in remaining pliable after freeze drying or drying such as glycerol, carboxy methyl cellulose or materials that protect against the damaging effects of radiation. Also, the mechanically useful substances may include structurally enhancing materials which are thermally or chemically set such as polymers and the like. Thus cryoprotectants, radiation protectants, plasticizers or liquid polymers may be added to the tissue cavities to enhance the tissue.

EXAMPLES

Example 1

Cortical bone cross sections which were cut from a human femur and a tibia, with a thickness of about 20 mm, were put in a swinging bucket centrifuge oriented such that the medullary canals of the bone pieces were oriented along the axis of the bucket (so forming an angle of 90 degrees with respect to the axis of rotation). The bone was placed on a shelf support (made from screen) inside the centrifuge bucket so that the separated or soluble material may fall away from the bone. The bone was spun dry for 10 minutes at 7500 RPM, then spun with dyed alcohol for 10 minutes at 7500 RPM. Penetration of the dye in the internal spaces of the bone sections was >99% as measured by histological cross-section analysis.

Example 2

Cortical bone cross sections cut from a human femur and a tibia, with a thickness of about 20 mm, were put in a swinging bucket centrifuge oriented such that the medullary canals of the bone piece were oriented perpendicular to the axis of the bucket (so forming an angle parallel with the axis of rotation). The bone was placed on a shelf support (made from screen) inside the centrifuge bucket so that the separated material could fall away from the bone. The bone was spun dry for 60 minutes at 7500 RPM, then spun with dyed alcohol for 60 minutes at 7500 RPM. Penetration of the dye was >99% as measured by histological cross-section analysis.

Example 3

Cortical bone cross sections were cut from a human femur and a tibia, with a thickness of about 20 mm, were put in a centrifuge with a rotor having a fixed angle of 22 degrees. The bone pieces were placed with their medullary canals oriented parallel with the axis of the bucket (so forming an angle of 22 degrees with respect to the axis of rotation). The bone was placed on a shelf support (made from screen) inside the centrifuge bucket so that the separated material fell away from the bone during centrifugation. The bone was spun dry for 10 minutes at 7500 RPM, then spun with dyed alcohol for 10 minutes at 7500 RPM. Penetration of the dye was 100% as measured by histological cross-section analysis.

Example 4

The experiment of Example 1 was repeated twice, only this time a dyed, 250 ppm solution of Triton-X 100 non-ionic surfactant in water was used instead of alcohol. Both runs yielded 99% or greater dye penetration as measured by histological cross-section analysis.

Example 5

The experiment of Example 2 was repeated, only this time a dyed, 250 ppm solution of Triton-X 100 brand non-ionic surfactant in water was used instead of alcohol. The dye penetration was >99% as measured by histological cross-section analysis.

Example 6

The experiment of Example 3 was repeated, only this time a dyed, 250 ppm solution of Triton-X 100 brand non-ionic surfactant in water was used instead of alcohol. The dye solution penetration was 98.6% as measured by histological cross-section analysis.

Example 7

The experiment of Example 4 was repeated at a lower speed and G force (870 G, 2500 RPM). After dry spinning for 1 hour and with the Triton-X 100 brand solution spinning for 5 minutes, penetration was measured. Only 64% dye penetration was noted as measured by histological cross-section analysis.

The time/RPM relationship to obtain cleaning during the "dry spin" cycle was determined by experiments with cortical bone. Cortical bone was chosen over cancellous bone because cortical bone is denser more difficult to penetrate and as such, represents a "worst case". The spin process removed water based fluids such as blood and tissue fluids, as well as some lipid as measured by weight loss and Soxlet extraction analysis of lipid from. bone samples which were taken before and after centrifugation.

Example 8

Bone, as used in experiment 1, was weighed, put in a swinging bucket centrifuge, and dry spun for varying times and at varying RPM. The bone reached a fixed moisture content of about 9 percent as measured by Carl Fischer titration, no matter what the G force within the range of 400 G to 4000 G used. Times to reach this weight varied from 10 minutes at the lowest G force to <5 minutes at the highest G force.

Example 9

Cortical bone rings, cut from tibia and femur rings were immersed in a 250 ppm Triton-X 100 brand surfactant solution and dye bath in an ultrasonic cleaner. The cleaner was operated at a frequency of about 40 KHz for one hour. Penetration of the dye ranged from 3% to 49%. This is much inferior to the >99% penetration with the dye and Triton-X 100 brand solution after 10 minutes in the centrifuge of Example 4.

Example 10

Weighed cancellous bone blocks were put in a swinging bucket centrifuge, and dry spun for varying time intervals at 5000 RPM. The lipid contents of the spun bone were measured and compared to that of untreated, control samples as measured by Soxlet extraction analysis of lipid from bone samples taken before and after centrifugation.

The controls contained 24% lipid by weight. This dropped to about 3% by 10 minutes and to about 2% by 30 minutes as measured by Soxlet extraction of lipid from bone samples taken before and after centrifugation.

Example 11

Biological materials such as connective tissues and bone are treated using the invention described herein to more rapidly inactivate or remove pathogens, introduce radiation protectants, cryoprotectants, mechanically useful substances, biologically useful substances or biologically active agents into the biological material such as tissue prior to or during the sterilization process compared to the previous methods.

For example, a piece of a bone or a whole bone as indicated in column 1 of the table below, with a length as indicated in column 2, is placed in a centrifuge. The bone or piece of bone is placed on a shelf support (made from screen) or a filter paper, inside the centrifuge bucket so that the separated or soluble material may fall away from the bone. The bone is spun dry with any of the one parameters as indicated in column 3 and any one of the parameters indicated in column 4 of the table below, then it is spun with the desired dyed solution, solvent or other liquid again with any of the one parameters as indicated in column 3 and any one of the parameters indicated in column 4 of the table below. Penetration of the dye solution, solvent or other liquid in to the internal spaces of the bone or bone fragments is at least any one of the values indicated in column 5 of the table below. In all cases penetration is measured by histological analysis.

| 1. Bone or fragment treated | 2. Bone length (centimeters) | 3. G force used for all bone or bone fragments | 4. Centrifuge time used for all bone or bone fragments | 5. Minimum Penetration of Solution into bone or fragments |
|---|---|---|---|---|
| Femur | 42-46 | About 500 G | 1 minute | At least 25% |
| Tibia | 37-41 | About 1,000 G | 5 minutes | At least 35% |
| Humerus | 30-34 | At least 1,500 G | 10 minutes | At least 45% |
| Radius | 23-24 | At least 3,000 G | 15 minutes | At least 75% |
| Ulna | 24-26 | At least 5,000 G | 30 minutes | At least 75% |
| Fibula | 34-41 | At least 7,500 G | 1 hour | At least 90% |
| Any bone fragment | 0.0005 cm to 46 cm | At least 10,000 G | 2 hours | At least 99% |

While various embodiments have been described, it will occur to one of ordinary skill that modifications may be made to the disclosed embodiments. It is intended that the scope of the invention be defined by the appended claims.

Appendix A

The biologically active agents that may be present in the solutions or solvents in present invention are any substances having biological activity, including small molecules, chemical compounds, proteins, polypeptides, polynucleotides, nucleoproteins, polysaccharides, glycoproteins, lipoproteins, and synthetic and biologically engineered analogs thereof.

Examples of biologically active compounds that might may comprise the solutions in present invention include literally any hydrophilic or hydrophobic biologically active compound. Preferably, though not necessarily, the drug is one that has already been deemed safe and effective for use by the appropriate governmental agency or body. For example, drugs for human use listed by the FDA under 21 C. F. R. 330.5, 331 through 361; 440-460; drugs for veterinary use listed by the FDA under 21 C. F. R. 500-582, incorporated herein by reference, are all considered acceptable for use in the present novel polymer networks.

Drugs that are not themselves liquid at body temperature can be incorporated into and may comprise the solutions in present invention and other polymers. Moreover, peptides and proteins which may normally be lysed by tissue-activated enzymes such as peptidases, can be passively protected in polymers or may comprise the solutions in present invention.

The term "biologically active compound" includes pharmacologically active substances that produce a local or systemic effect in animals, plants, or viruses. The term thus means any substance intended for use in the diagnosis, cure, mitigation, treatment or prevention of disease or in the enhancement of desirable physical or mental development and conditions in an animal, plant, or virus. The term "animal" used herein is taken to mean mammals, such as primates, including humans, sheep, horses, cattle, pigs, dogs, cats, rats, mice; birds; reptiles; fish; insects; arachnids; protists (e. g. protozoa); and prokaryotic bacteria. The term "plant" means higher plants(angiosperms, gymnosperms), fungi, and prokaryotic blue-green "algae" (i. e. cyanobacteria).

The biologically active compound may be any substance having biological activity, including proteins, polypeptides, polynucleotides, nucleoproteins, polysaccharides, glycoproteins, lipoproteins, and synthetic and biologically engineered analogs thereof. The term "protein" is art-recognized and for purposes of this invention also encompasses peptides. The proteins or peptides may be any biologically active protein or peptide, naturally occurring or synthetic. Examples of proteins include antibodies, enzymes, steroids, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules.

Classes of biologically active compounds which can be loaded into crosslinked gels using the methods of this invention include, but are not limited to, anti-AIDS substances, anti-cancer substances, antibiotics, immunosuppressants (e.g., cyclosporine) anti-viral substances, enzyme inhibitors, neurotoxins, opioids, hypnotics, antihistamines, lubricants tranquilizers, anti-convulsants, muscle relaxants and anti-Parkinson substances, anti-spasmodics and muscle contractants, miotics and anti-cholinergics, anti-glaucoma compounds, anti-parasite and/or anti-protozoal compounds, anti-hypertensives, analgesics, anti-pyretics and anti-inflammatory agents such asNSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

A more complete listing of classes of compounds suitable for loading into polymers using the present methods may be found in the Pharmazeutische Wirkstoffe (Von Kleemann et al.(eds) Stuttgart/New York, 1987, incorporated herein by reference).

Examples of particular biologically active substances are presented below: Anti-AIDS substances are substances used to treat or prevent Autoimmune Deficiency Syndrome (AIDS). Examples of such substances include CD4,3'-azido-3'-deoxythymidine (AZT), 9-(2-hydroxyethoxymethyl)-guanine acyclovir, phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms.

Examples of antibiotics include penicillin, tetracycline, chloramphenicol, minocycline, doxycycline, vanomycin, bacitracin, kanamycin, neomycin, gentamycin, erythromicin and cephalosporins.

Anti-viral agents are substances capable of destroying or suppressing the replication of viruses. Examples of anti-viral agents include a-methyl-P-adamantanemethylamine, 1,-D-ribofuranosyl-1,2,4-triazole-3 carboxamide, 9-[2-hydroxyethoxy]methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine, I-hydroxy maleate, iodotubercidin, p-bromotetramisole, 10-(alpha-diethylaminopropionyl)-phenothiazine hydrochloride, calmidazolium chloride, hemicholinium-3,3,5-dinitrocatechol, diacylglycerol kinase inhibitorI, diacylglycerol kinase inhibitor II, 3-phenylpropargylamine, N6-monomethyl-L-arginine acetate, carbidopa, 3-hydroxybenzylhydrazine HCl, hydralazine HCl, clorgyline HCl, deprenylHCl, L(−)-, deprenylHCl, D(+)-, hydroxylamine HCl, iproniazid phosphate, 6-MeO-tetrahydro-9H-pyrido-indole, nialamide, pargyline-HCl, quinacrineHCl, semicarbazide HCl, tranylcypromine HCl, N,N-diethylaminoethyl-2,2-diphenylvalerate hydrochloride, 3-isobutyl-1-methylxanthne, papaverineHCl, indomethacind, 2-cyclooctyl-2-hydroxyethylamine hydrochloride, 2,3-dichloro-a-methylbenzylamine (DCMB), 8,9-dichloro-2,3,4,5-tetrahydro-IH-2-benzazepine hydrochloride, p-aminoglutethimide, p-aminoglutethimide tartrate, R(+)-, p-aminoglutethimide tartrate, S(−)-, 3-iodotyrosine, alpha-methyltyrosine, L-, alpha-methyltyrosine, D L-, acetazolamide, dichlorphenamide, 6-hydroxy-2-benzothiazolesulfonamide, and allopurinol.

Neurotoxins are substances, which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4-phenyl-1,2,5,6tetrahydropyridine HCl, 1-methyl-4-phenylpyridinium iodide.

Opioids are substances having opiate like effects that are not derived from opium.

Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimineHCl, buprenorphine, chlornaltrexamine2HCl, funaltrexamione HCl, nalbuphine HCl, nalorphine HCl, naloxone HCl, naloxonazine, naltrexone HCl, andnaltrindole HCl.

Hypnotics are substances, which produce a hypnotic effect. Hypnotics include pentobarbital sodium, phenobarbital, secobarbital, thiopental and mixtures, thereof, heterocyclichypnotics, dioxopiperidines, glutarimides, diethyl isovaleramide, a-bromoisovaleryl urea, urethanes and disulfanes.

Antihistamines are substances which competitively inhibit the effects of histamines.

Examples includepyrilamine, chlorpheniramine, tetrahydrazoline, and the like. Lubricants are substances that increase the lubricity of the environment into which they are delivered. Examples of biologically active lubricants include water and saline.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, Chk andethosuximide.

Muscle relaxants and anti-Parkinson agents are agents which relax muscles or reduce or eliminate symptoms associated with Parkinson's disease. Examples of such agents includemephenesin, methocarbomal, cyclobenzaprine hydrochloride, trihexylphenidyl hydrochloride, levodopa/ carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics andanti-cholinersics are compounds which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma compounds includebetaxalol, pilocarpine, timolol, timolol salts, and combinations of timolol, and/or its salts, with pilocarpine.

Anti-parasitic, -protozoal and-fungals include ivermectin, pyrimethamine, trisulfapyrimidine, clindamycin, amphotericin B, nystatin, flucytosine, natamycin, and miconazole.

Anti-hypertensives are substances capable of counteracting high blood pressure.

Examples of such substances include alpha-methyldopa and the pivaloyloxyethyl ester of alpha-methyldopa.

Analgesics are substances capable of preventing, reducing, or relieving pain. Examples of analgesics include morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include aspirin (salicylic acid), indomethacin, sodium indomethacintrihydrate, salicylamide, naproxen, colchicine, fenoprofen, sulindac, diflunisal, diclofenac, indoprofen and sodium salicylamide.

Local anesthetics are substances which have an anesthetic effect in a localized region.

Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, pheneizine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includesdramamine.

Imaging agents are agents capable of imaging adesired site, e.g. tumor, in vivo. Examples of imaging agents include substances having a label which is detectable in vivo, e. g. antibodies attached to fluorescent labels. The term antibody includes whole antibodies or fragments thereof.

Specific targeting agents include agents capable of delivering a therapeutic agent to a desired site, e. g. tumor, and providing a therapeutic effect. Examples of targeting agents include agents which can carry toxins or other agents which provide beneficial effects.

The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (PDGF). Other chemotactic factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derivedendothelial cell growth factor, insulin-like growth factor, nerve growth factor, and bonegrowth/cartilage-inducing factor (alpha and beta), or other bone morphogenetic protein.

Other cell response modifiers are the interleukins, interleukin inhibitors or interleukin receptors, including interleukin 1 through interleukin 10; interferons, including alpha, beta and gamma; hematopoietic factors, includingerythropoietin, granulocyte colony stimulating factor, macrophage colony stimulating factor and granulocyte-macrophage colony stimulating factor; tumor necrosis factors, including alpha and beta; transforming growth factors (beta), includingbeta-1, beta-2, beta-3, inhibin, and activin; and bone morphogenetic proteins including all BMPs.

What is claimed:

1. A process for inactivating and/or reducing pathogens from tissue having a plurality of cavities in which pathogens reside comprising:
    centrifuging the tissue in a centrifuge with a flowing pathogen solvent reducing solution wherein the solution is flowed continuously to and away from the centrifuge containing the tissue during the centrifuging, the centrifuge producing a G force on the material to remove material from the tissue and promote penetration into the tissue;
    the centrifuging causing penetration of the pathogen reducing solution into substantially all of the cavities of the tissue where the pathogens reside to thereby inactivate and/or reduce the pathogen content in said cavities.

2. The process of claim 1 wherein the solvent fluid is selected from at least one of the group consisting of an alcohol, a detergent, an oxidizer, a solvent and a surfactant.

3. The process of claim 1 including exposing the tissue to a volume of said reducing solution of greater than 3 liters.

4. The process of claim 1 wherein the G force exceeds 1600 G.

5. The process of claim 1 including dry centrifuging the tissue after centrifuging the pathogen reducing solution to remove traces of solvents and debris.

6. The process of claim 1 wherein the tissue is at least one of cancellous bone, cortical bone, and connective tissue.

7. The process of claim 1 wherein the solvent reducing solution comprises at least one viral and/or bacterial pathogen inactivating solution to inactivate the pathogens.

8. The process of claim 1 wherein the solvent reducing solution is for inactivating viral and/or bacterial pathogens, the centrifuging for flowing the solvent reducing solution to flush the pathogens from the cavities and inactivate the pathogens in the cavities and then removing the solvent reducing solution carrying the flushed pathogens from the vicinity of the tissue.

9. The process of claim 1 wherein the tissue comprises bone, the pathogens comprise lipids and/or proteins, the solvent reducing solution for removing the lipids and/or proteins from the bone, the process comprising continuously flowing and centrifuging the pathogen reducing solvents and/or surfactants with the bone so that the solvents and/or surfactants continuously infuse into and out of the cavities of the bone to continuously flush the lipids and/or proteins from the bone.

10. The process of claim 1 wherein the tissue comprises bone, the pathogens comprise lipids and/or proteins in the tissue cavities, the process for solublizing the lipids and/or proteins by centrifuging the bone with the pathogen reducing solvent and/or surfactant to cause the pathogen reducing solvent and/or surfactant to flow into substantially all of the cavities of the tissue.

11. The process of claim 1 including infusing biologically and/or mechanically useful substances into the tissue cavities during a centrifuging step.

12. The process of claim 11 wherein the infusing step includes infusing at least one antibiotic for forming a tissue preservative during storage of the tissue.

13. The process of claim 11 wherein the infusing step includes infusing at least one antibiotic fonning a tissue preservative during storage of the tissue and at least one tissue growth factor for release from the tissue after implantation of the tissue into an animal.

14. The process of claim 11 wherein the infusing the mechanically useful substance step includes infusing plasticizer for maintaining the tissue pliability after freeze drying or drying.

15. The process of claim 11 wherein the infusing the mechanically useful substance step includes infusing glycerol to maintain the tissue pliability after freeze drying or drying.

16. The process of claim 11 wherein the infusing the mechanically useful substance step includes infusing structurally enhancing materials, which are thennally or chemically set.

17. The process of claim 11 wherein the infusing the mechanically useful substance step includes infusing polymers, which are thermally or chemically set.

18. The process of claim 1, further comprising infusing a chemically reactive substance during at least one further centrifuging step for breaking down lipids and/or proteins.

* * * * *

UNITED STATES PATENT AND TRADEMARK OFFICE
CERTIFICATE OF CORRECTION

PATENT NO. : 7,585,461 B2  Page 1 of 1
APPLICATION NO. : 10/766614
DATED : September 8, 2009
INVENTOR(S) : Shimp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1404 days.

Signed and Sealed this

Fourteenth Day of September, 2010

David J. Kappos
*Director of the United States Patent and Trademark Office*